United States Patent [19]

McBride et al.

[11] Patent Number: 5,254,607
[45] Date of Patent: Oct. 19, 1993

[54] BIODEGRADABLE, LIQUID IMPERVIOUS FILMS

[75] Inventors: Robert K. McBride, Jasonville; James M. Adams, Terre Haute; Peter I. Chang, Terre Haute; Carl D. Ray, Terre Haute, all of Ind.

[73] Assignee: Tredegar Industries, Inc., Richmond, Va.

[21] Appl. No.: 721,794

[22] Filed: Jun. 26, 1991

[51] Int. Cl.$^5$ .............................. C08L 3/04; C08L 3/06
[52] U.S. Cl. ..................................... 524/52; 524/47; 524/51; 524/53
[58] Field of Search .................. 524/47, 51, 52, 53

[56] References Cited

U.S. PATENT DOCUMENTS

| | | | |
|---|---|---|---|
| 3,867,324 | 2/1975 | Clendinning et al. | 260/23 |
| 3,901,838 | 8/1975 | Clendinning et al. | 260/23 |
| 3,922,239 | 11/1975 | Koleske et al. | 260/13 |
| 3,925,504 | 12/1975 | Koleske et al. | 260/823 |
| 3,931,068 | 1/1976 | Clendinning et al. | 260/7.5 |
| 3,949,145 | 4/1976 | Otey et al. | 428/423 |
| 4,016,117 | 4/1977 | Griffin | 260/17.4 |
| 4,021,388 | 5/1977 | Griffin | 260/13 |
| 4,133,784 | 1/1979 | Otey et al. | 524/52 |
| 4,337,181 | 6/1982 | Otey et al. | 524/47 |
| 4,372,311 | 2/1983 | Potts | 128/287 |
| 4,454,268 | 6/1984 | Otey et al. | 524/47 |
| 4,503,098 | 3/1985 | Potts | 427/394 |
| 4,826,493 | 5/1989 | Martini et al. | 604/327 |
| 4,873,270 | 10/1989 | Aime et al. | 524/52 |
| 4,880,592 | 11/1989 | Martini et al. | 264/514 |
| 4,983,651 | 1/1991 | Griffin | 524/47 |
| 5,026,363 | 6/1991 | Pratt | 604/385.1 |

FOREIGN PATENT DOCUMENTS

| | | | |
|---|---|---|---|
| 0326517 | 8/1989 | European Pat. Off. | 30/12 |
| 0327505 | 8/1989 | European Pat. Off. | 3/2 |
| 0400531 | 12/1990 | European Pat. Off. | 30/12 |
| 0400532 | 12/1990 | European Pat. Off. | 23/08 |
| 0408503 | 1/1991 | European Pat. Off. | 3/2 |
| 0409781 | 1/1991 | European Pat. Off. | 3/2 |
| WO9010671 | 9/1990 | PCT Int'l Appl. | 3/2 |
| WO9102023 | 2/1991 | PCT Int'l Appl. | 3/2 |
| WO9102024 | 2/1991 | PCT Int'l Appl. | 3/2 |
| WO9102025 | 2/1991 | PCT Int'l Appl. | 3/2 |
| 2214918 | 9/1989 | United Kingdom | 3/2 |

OTHER PUBLICATIONS

Estane ® Thermoplastic Polyurethane Compound Selection Guide, B. F. Goodrich ES-2B, B. F. Goodrich, 1987.
Pellethane ® Polyurethane Elastomers, Typical Physical Properties, Dow Chemical Company, (not dated).
Morthane ® Thermoplastic Polyurethanes for Extrusion, Morton International, 1991.

*Primary Examiner*—Paul R. Michl
*Assistant Examiner*—Peter Szekely
*Attorney, Agent, or Firm*—Emch, Schaffer, Schaub & Porcello Co.

[57] ABSTRACT

Liquid impervious, biodegradable films are disclosed. In particular, the films comprise a blend of an interpenetrated network of destructurized starch with ethylene/acrylic acid copolymers or ethylene/vinyl alcohol copolymers, and an aliphatic polyester such as polycaprolactone. Diapers, sanitary napkins, pantiliners, and the like, containing backsheets prepared from the foregoing materials are also disclosed.

13 Claims, No Drawings

BIODEGRADABLE, LIQUID IMPERVIOUS FILMS

TECHNICAL FIELD

The present invention relates to liquid impervious films comprising a blend of biodegradable, thermoplastic polymers. The films are especially suitable for use as backsheets in absorbent articles such as diapers, sanitary napkins, pantiliners, and the like, which are adapted for absorbing various bodily fluids. The films herein may also be used in a variety of product applications such as agricultural mulch film, heat-sealable packaging film, plastic garbage bags, etc.

BACKGROUND OF THE INVENTION

A wide variety of absorbent structures designed to be efficient for the absorption of body fluids such as blood, urine, menses, and the like, are known. Disposable products of this type generally comprise some sort of fluid-permeable topsheet material, an absorbent core, and a fluid-impermeable backsheet material.

Heretofore, such absorbent structures have been prepared using, for example, topsheet materials prepared from woven, nonwoven, or porous formed-film polyethylene or polypropylene materials. Backsheet materials typically comprise flexible polyethylene sheets. Absorbent core materials typically comprise wood pulp fibers or wood pulp fibers in combination with absorbent gelling materials.

One aspect of such sanitary products that has recently been considered is their disposability. Although such products largely comprise materials that would be expected ultimately to degrade, and although products of this type contribute only a very small percentage of the total solid waste materials generated by consumers each year, nevertheless, there is currently a perceived need to devise such disposable products from materials that degrade relatively quickly, thereby lessening their bulk, and also increasing the compostability of the disposable products.

A conventional disposable absorbent product is already to a large extent biodegradable. A typical disposable diaper, for example, consists of about 80% biodegradable materials, e.g., wood pulp fibers, and the like. Nevertheless, as mentioned above there is a need for reducing the amount of non-biodegradable materials in disposable absorbent articles. There is a particular need to replace polyethylene backsheets in absorbent articles with liquid impervious films comprised of biodegradable materials, because the backsheet is typically the largest non-biodegradable component of an absorbent article.

BACKGROUND ART

Degradable mulch films comprising starch, poly (vinyl alcohol) and glycerol are disclosed in U.S. Pat. No. 3,949,145, Otey and Mark, issued Apr. 6, 1976. The degradability of the films is controlled by application of a non-degradable water resistant coating based on mixtures of polyol-toluene diisocyanate prepolymers with poly(vinylidene chlorideacrylonitrile) copolymers or poly (vinyl chloride) resins mixed with plasticizers.

Degradable mulch films with improved moisture resistance and comprising starch and ethylene/acrylic acid copolymers are disclosed in U.S. Pat. No. 4,133,784, Otey and Westhoff, issued Jan. 9, 1979, and U.S. Pat. No. 4,337,181, Otey and Westhoff, issued Jun. 29, 1982. The films disclosed in the latter patent also include a neutralizing agent such as ammonia, which allows them to be processed by blown film technology with good properties. Polyethylene is specified as an optional component in the films. Applications such as garbage bags and various types of packaging are al so contemplated in U.S. Pat. No. 4,337,181.

International Patent Application WO90/10671 discloses biodegradable articles based on starch. In particular, destructurized starch and ethylene acrylic acid copolymer are combined to form an interpenetrating network. It has also been found that an ethylene vinyl alcohol copolymer can be used in place of the ethylene acrylic acid copolymer, as will be discussed hereinafter.

The interpenetrated networks of destructurized starch described in the above reference are thermoplastic in nature and can be processed by both cast film and blown film extrusion processes into strong, tough films. These films can be employed to make biodegradable backsheets for use in disposable absorbent articles. However, such films tend to exhibit sensitivity to ambient humidity, especially where the starch concentration is greater than about 50% by volume of the total film. It has been found, for example, that the modulus of films comprised only of the interpenetrated network of destructurized starch and ethylene vinyl alcohol copolymer decreases by about 50% as the relative humidity changes from about 20% to about 90%. Although such sensitivity to humidity is a reversible process, it makes the film inconsistent on a day-today basis to the degree that converting operations and end user performance can be negatively affected.

It has also been found that films comprised of the interpenetrated network of destructurized starch are sensitive to loss of plasticizers, water, urea, and other low molecular weight components. Loss of these components can occur, for example, when an absorbent batt of paper fibers is placed in contact with the film. The loss of such components in this case is irreversible, and greatly decreases the strength and toughness of the film. The loss of strength and toughness can be great enough to cause the film to fail even under the limited stresses applied by end users of the absorbent article.

Furthermore, films made from only the interpenetrated network are highly permeable to water vapor. This is beneficial in some applications where breathability is desirable in the absorbent article. However, high water vapor permeability may not be desirable if the absorbent article is required to contain large quantities of fluids, such as in the case of a diaper. High water permeation can lead to excessive condensation on the outside of the diaper leaving it feeling cold and wet to the touch.

In achieving the present invention, it was found that the addition of other thermoplastic polymers and copolymers to the interpenetrated network of destructurized starch and ethylene acrylic acid copolymer or ethylene vinyl alcohol copolymer can substantially reduce the humidity sensitivity, the loss of properties due to the migration of low molecular weight components, and the moisture vapor permeation rate. However, it was also discovered that the addition of conventional non-biodegradable polymers (e.g., polyethylene) invariably slows down the rate of biodegradation, and hence the compostability of films containing the non-biodegradable polymers. The present invention involves the addition of biodegradable aliphatic polyesters to the interpenetrated network of destructurized starch to achieve absorbent articles with biodegradable backsheets that are not overly sensitive to changes in ambient humidity or contact with absorbent media, and that have sufficiently low water permeation rates to prevent condensation on the outside of the backsheet.

It is an object of the present invention to provide absorbent articles having a liquid impervious backsheet comprising a mixture of biodegradable polymers. It is a particular object of the present invention to provide such products wherein the biodegradable polymers are derived from combinations of interpenetrated networks of destructurized starch, aliphatic polyesters, and optionally, polyolefins.

It is also an object of the present invention to provide a biodegradable film which is suitable for a variety of product applications such as agricultural mulch film, heat-sealable packaging films, plastic garbage bags, etc.

SUMMARY OF THE INVENTION

The present invention encompasses disposable absorbent articles comprising a liquid pervious topsheet, a liquid impervious backsheet and an absorbent core encased between the topsheet and the backsheet, said articles being characterized in that said backsheet comprises a flexible biodegradable film comprising a mixture of an interpenetrating network of destructurized starch with ethylene/acrylic acid copolymers or ethylene/vinyl alcohol copolymers, and an aliphatic polyester. Optionally, the biodegradable film may further comprise a polyolefin material. The biodegradable polymers are combined in various ways to impart specific performance properties to the backsheet. Examples of such absorbent articles include disposable diapers, adult incontinent pads, sanitary napkins and pantiliners. The present invention also encompasses liquid impervious, biodegradable films per se comprised of the above mentioned mixture of components.

DETAILED DESCRIPTION OF THE INVENTION

The films used to prepare the backsheet materials and the other biodegradable products employed herein are derived from blends of two or more polymeric components. The components are chosen so as to render the film blends biodegradable. In general, the films used in the present invention comprise blends of an interpenetrated network of destructurized starch with ethylene/acrylic acid copolymers or ethylene/vinyl alcohol copolymers and an aliphatic polyester. Optional ingredients that also can be used in the polymer blends of the present invention include certain polyolefins. Each of these components is described in detail below.

A. Destructurized Starch

The biodegradable films of the present invention contain a first component based on an interpenetrated network of destructurized starch with an ethylene/acrylic acid copolymer or an ethylene/ vinyl alcohol copolymer (hereinafter referred to as the destructurized starch component). A detailed description of these materials can be found in International Patent Application WO 90/10671, Bastioli, et al., published Sep. 20, 1990, and European Patent Application 0 408 503 A2, Silbiger et al., published Jan. 16, 1991, both of which are incorporated by reference herein. The WO90/10671 reference generally describes, at pages 4-7, "an interpenetrated network of destructurized starch and a polymer" as follows:

The product of the interaction between starch and EAA copolymer is obtained in situ during the conversion process of the starting products to the formed article.

Preferably the ethylene acrylic acid copolymer (EAA) has an acrylic acid content ranging from 3 to 30% by weight and the destructurized starch phase which is not bound to the EAA copolymer, is finely and uniformly dispersed in the mix in the form of particles having an average number diameter below 1 micron and a dispersion of the particles sizes below 3 microns.

The dispersion of the destructurized starch particles dimensions is determined by the ratio between the average number diameter and the average surface diameter.

The proportion of the various components of the composition may vary as a function of the properties to be obtained, of the temperature and of the forming process. Generally, formed articles and films having excellent physical-mechanical characteristics and insolubility in water contain:

from 10 to 90% by weight of a total destructurized starch;

from 10 to 90% by weight of a total EAA copolymer having an acrylic acid content ranging from 3 to 30% by weight; and from 0 to 6% of water.

wherein less than 40% and preferably less than 20% by weight of the total starch is free and in the form of particles having an average number diameter below 1 micron, while the remaining starch is bound to the EAA copolymer to form the IPN (interpenetrated network) product.

The formed articles and films may also contain urea, which is added to the starting mix in order to improve the processability thereof. The urea amount, if any, does not exceed 30% by weight and preferably ranges from 5 to 20% by weight referred to the mix.

The water content of the articles is generally lower than the one which is generally present in the starch. Usually, the water content does not exceed 6% by weight and it may be also fully absent.

The ammonia, which is optionally added to the starting mix in order to improve the preparation of the composition is removed either during the extrusion process or subsequently, during a drying step, wherefore the articles generally do not contain ammonia, or the ammonia content does not exceed, at the most, 0.5% by weight with respect to the mix.

The process for producing the formed articles and films comprises mixing the components of the mix containing starch, an EAA copolymer, in a starch/EAA copolymer weight ratio ranging from 1:9 to 9:1 water, and optionally urea and ammonia, in an extruder heated to a temperature ranging from 90° to 150° C., bringing the water content to a value below 6% by weight and the ammonia content to a value below 0.5% by weight.

The reduction of the water content prior to the further processing of the composition constitutes an important feature of the process according to the WO90/10671 invention.

The reduction of the water content and optionally of the ammonia contents can be carried out either by venting, directly in the extruder, or by drying at about 70°-100° C. in an air flow or under vacuum after the extrusion step.

According to a preferred method for the preparation of the formed articles and films of the WO90/10671 invention, the reduction of the water content is carried out in an intermediate degassing stage of the extrusion process.

Accordingly, this preferred method comprises supplying to an extruder heated to a temperature of between 90° and 150° C. a material including starch and an ethylene-acetic acid copolymer in a starch/copolymer ratio of from 1:9 to 9:1, and a quantity of water of from 10 to 25% of the weight of the starch component and subjecting the supplied material to the following sequence:
- a first stage in which the starch supplied is intimately mixed with the copolymer until it is substantially destructurized and interpenetrated,
- a stage in which the material output from the mixing step is degassed to reduce its water content to no more than 2% by weight of the weight of the composition, and
- a stage in which the degassed material is transported and compressed at a pressure greater than 500 Pa and the material is extruded at a temperature of between 105° and 130° C.

Upstream of the first mixing stage, the material supplied is preferably subjected to a transportation stage during which the temperature of material is increased progressively to between 60° and 100° C.

The subsequent mixing stage is carried out at a temperature preferably of between 105° and 140° C. under such conditions that the starch is at the same time substantially destructurized and interpenetrated.

The phenomena which take place in this stage and which lead to the destructurization of the starch are known and are generally explained by the creation of disorder in the molecular structure of the starch particles as a result of heat treatment carried out above the glass-transition temperature and melting points of its components.

The degassing stage may typically include from 1 to 4 degassing zones in which the body of the extruder is brought to a subatmospheric pressure, generally between 690 and 700 mm Hg. In this stage, the quantity of water can be reduced to values of from 2 to 0.1, preferably below 1. The degassing is carried out with the use of one or more water ring pumps of known type.

The degassed material then goes through a further transportation stage constituted by conveyor elements alone, or by mixing elements followed by conveyor elements, to improve the interpenetration and prevent the blend from losing the uniformity achieved during the first mixing stage. The biodegradable films of the present invention preferably comprise greater than 50%, more preferably, from about 55% to about 95% and, most preferably, from about 60% to about 85% by weight of the destructurized starch component.

The destructurized starch component preferably comprises a) a phase of destructurized starch in the form of particles each having an average number diameter lower than 1 micrometer; b) a phase of a copolymer of ethylene and acrylic acid (EAA) or a copolymer of ethylene and vinyl alcohol (EVOH); c) a phase consisting of an interpenetrated network (IPN) product resulting from the interaction between starch and the EAA or EVOH copolymer; and optionally, water in an amount lower than 6%, preferably lower than 2% by weight with respect to the total composition. One preferred material of this kind comprises from 10 to 90% by weight of a total destructurized starch; from 10 to 90% by weight of a total EAA copolymer having an acrylic acid content ranging from 3 to 30% by weight and from 0 to 6% of water, wherein less than 40% and preferably less than 20% by weight of the total starch is free and in the form of particles having an average number diameter below 1 micrometer, while the remaining starch is bound to the EAA copolymer to form said IPN product.

Another preferred material of this kind comprises from 10 to 90% by weight of a total destructurized starch; from 1 to 60% by weigh of a total ethylene vinyl alcohol copolymer having a vinyl alcohol content ranging from about 50 to about 80 mole %; and from 0 to 10% by weight of water, wherein less than 40% and preferably less than 20% by weight of the total starch is free and in the form of particles having an average number diameter below 1 micrometer, while the remaining starch is bound to the EVOH copolymer to form said IPN product.

An example of a commercially available destructurized starch component suitable for use in the present invention is Mater-Bi, marketed by Novamont.

The destructurized starch component may also contain other ingredients such as plasticizers, humectants, and other low molecular weight compounds. Typical plasticizers include polar organic compounds such as urea, glycerol, glycerol monoesters, sorbitol, sorbitol esters and ethers, and glycols such as propylene glycol, mono-, di- and triethylene glycols. For a more detailed description of the types of additives that may be added is to starch, see *Handbook of Water-Soluble Gums and Resins*, Robert L. Davidson, Editor, McGraw Hill Company (1980) Chapter 22, pages 68-69.

B. Aliphatic Polyester

The biodegradable films of the present invention preferably comprise from about 5% to about 45%, more preferably, from about 15% to about 40% by weight of an aliphatic polyester. As used herein, the term aliphatic polyester refers to the family of saturated polyesters which are generally acknowledged as biodegradable. A detailed description of the various types of aliphatic polyesters suitable for use in the present invention is provided hereinafter.

Although some types of aliphatic polyesters can be processed directly into thin water resistant films, their melting points may be too low to be used alone as backsheets for disposable absorbent articles. In other cases, the film's mechanical strength may not be sufficient for use as backsheets. In yet other cases, the crystallization rate of aliphatic polyesters are too slow to permit film processing from the melt state.

Polycaprolactone is an example of a preferred biodegradable aliphatic polyester for use in .the present invention. It is produced via the ring opening polymerization of epsilon-caprolactone, a seven-membered ring compound. As described in Union Carbide Brochure F-60456 entitled "Tone Polymers", the polymerization is initiated with a diol (HO—R—OH, where R is an aliphatic segment) to produce polymers with the following structure:

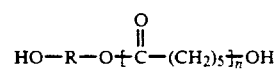

where n is the degree of polymerization.

Polycaprolactone polymers are available from Union Carbide Corporation under the tradename TONE in a variety of molecular weight grades. For example, TONE polymers P-300 and P-700 have degrees of polymerization of about 95 and 400 respectively, corresponding to molecular weights of about 10,000 and 40,000. TONE P-767 is prepared from a special high purity grade of caprolactone monomer and has an average molecular weight of about 43,000. TONE P-787 has an even higher average molecular weight of about 80,000.

Polycaprolactone polymers having molecular weights of about 40,000 and greater can be melt processed into strong water resistant films. Except for their low melting point of about 60° C. (140° F.), these films could function as backsheets for absorbent articles. Because of their low melting points, backsheets consisting of 100% polycaprolactone would have difficulty withstanding the high temperatures encountered when hot glue is applied to the diaper during the manufacturing process. In addition, during shipping and/or warehouse storage, temperatures of 60° C. are often reached. Backsheets consisting of 100% polycaprolactone would be difficult to stabilize in such an environment and might distort, stick to one another, or even melt.

In the present invention, polycaprolactone polymers having an average molecular weight of 40,000 or more are preferred for blending with the starch interpenetrated network. Especially preferred are polycaprolactone polymers having an average molecular weight of about 80,000 grams per mole (e.g., TONE P-787).

Other types of aliphatic polyesters suitable for use in the present invention are derived from the reaction of an aliphatic dicarboxylic acid and a diol. As described in "An Overview of Plastics Degradability", by Klemchuk, published in MODERN PLASTICS (August, 1989) and incorporated herein by reference, many of these polyesters are biodegradable since they are susceptible to enzymatic hydrolysis. Moreover, the acid and alcohol fragments of the hydrolysis are also easily assimilated by microorganisms.

Such polyesters are prepared via the generalized reaction shown below:

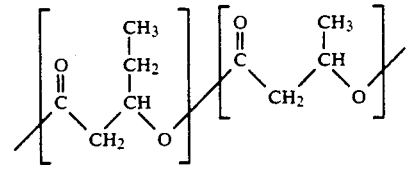

DIOL     DICARBOXYLIC ACID

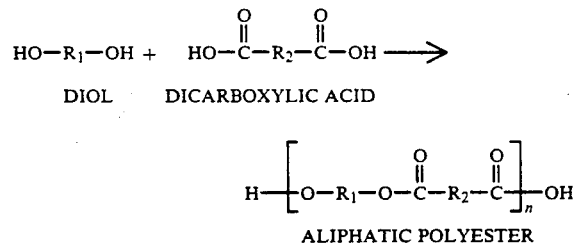

ALIPHATIC POLYESTER where $R_1$ is a linear methylene chain $-(CH_2-)_x$ with $2 \leq X \leq 10$, $R_2$ is also a linear methylene chain $-(CH_2-)_y$ with $2 \leq Y \leq 10$; and n is the degree of polymerization. Examples of these types of aliphatic polyesters include:

Polyethylene adipate where x=2 and y=4;
Poly (1,3 propanediol adipate) where x=3 and y=4;
Poly (1,4 butanediol adipate) where x=4 and y=4;
Polyethylene sebacate where x=2 and y=8;
Poly (1,4 butanediol sebacate) where x=4 and y=8;
Poly (1,3 propanediol succinate) where x=3 and y=2;
Poly (1,4 butanediol glutarate) where x=4 and y=3.

Biodegradable polyurethanes can be prepared from low molecular weight aliphatic polyesters derived from epsilon-caprolactone or the reaction products of a diol-dicarboxylic acid condensation. In general, these polyesters have molecular weights less than 10,000 grams per mole and frequently as low as 1000 to 2000 grams per mole. Examples of biodegradable polyester urethanes derived from polyethyleneglycol adipate, poly (1,3-propanediol) adipate and poly (1,4-butanediol adipate) are disclosed in "The Prospects for Biodegradable Plastics" by F. Rodriguez (Chem Tech, July - 1971) incorporated herein by reference. For purposes of the present invention, biodegradable polyurethanes prepared from aliphatic polyesters are considered to be aliphatic polyesters and are suitable for use herein.

Poly (alpha-hydroxy alkanoates)

Another family of biodegradable aliphatic polyesters includes those derived from alpha-hydroxy carboxylic acids. This family of poly(alpha-hydroxy alkanoates) includes synthetic polymers such as polylactates from lactic acid and naturally derived polymers such as polyhydroxybutyrate (PHB) polymers and polyhydroxybutyrate-valerate (PHBV) copolymers. Preferred examples of polyhydroxybutyrate homopolymer and polyhydroxy butyrate valerate copolymers are described in U.S. Pat. No. 4,393,167, Holmes et al., issued Jul. 12, 1983 and U.S. Pat. No. 4,880,592, Martini et al., issued Nov. 14, 1989, both references incorporated herein by reference. PHBV copolymers have the generalized structure shown below.

Hydroxyvalerate (HV)     Hydroxybutyrate (HB)

Such copolymers are commercially available from Imperial Chemical Industries under the tradename BIOPOL. The BIOPOL polymers are produced from the fermentation of sugar by the bacterium Alcaligenes eutrophus. PHBV polymers are currently produced with valerate contents ranging from about 5 to about 24 mole percent. Increasing valerate content decreases the melting point, crystallinity, and stiffness of the polymer. An overview of BIOPOL technology is provided in BUSINESS 2000+, (Winter, 1990), incorporated herein by reference.

Unfortunately, PHBV copolymers are difficult to process directly into films because of their slow crystallization rate. However, it is known that they blend well with some synthetic homopolymers containing polar groups such as polyvinylchloride and polycarbonate and that the blends can be processed into useful films. In achieving the current invention, it was surprisingly found that PHBV polymers could also be blended with the starch interpenetrated network and extruded into biodegradable films. PHBV copolymers containing from about 10 to about 24 mole percent valerate are preferred because their melting points are low enough to permit melt processing of the blends below the thermal degradation point of the starch component which is about 160° C.

Still another type of aliphatic polyester suitable for use in the present invention are those derived from the oxidation reaction of ethylene-carbon monoxide copolymers with peroxyacid oxidizing agents. Preferred examples of these materials are described in U.S. Pat. No. 4,929,711, Chang et al., issued May 29, 1990 and U.S. Pat. No. 4,957,997, Chang et al., issued Sep. 18, 1990, incorporated herein by reference.

C. Polyolefins

Additional components based on polyolefins and polyolefin copolymers may also be included in the film blends of the present invention. Preferred examples of polyolefins for use herein include polyethylene, polypropylene, ethylene/propylene copolymers, ethylene/vinyl acetate copolymers, ethylene/acrylic acid copolymers, ethylene/methacrylic acid copolymers, ethylene/acrylic ester copolymers, ethylene/carbon monoxide copolymers, and ethylene/vinyl alcohol copolymers. Other examples of suitable polyolefins include poly styrene, poly (vinyl acetate), poly (1-butene), poly (2-butene), poly (1-pentene), poly (2-pentene), poly (3-methyl-1-pentene), poly (4-methyl-1-pentene), 1,2-poly-1,3-butadiene, 1,4-poly-1,3-butadiene, polyisoprene, polychloroprene, ethylene-ethyl acrylate, ethylene-methyl acrylate, ethylene-butyl acrylate, polybutylene, Ionomer, maleic anhydride modified copolymers and homopolymers, and the like. The films of the present invention may contain from 1% to about 40% by weight of these polyolefins, and more preferably from 1% to about 33% by weight of the polyolefin materials.

Optional Components

In addition to the above-mentioned components, the biodegradable films of the present invention may contain other components as may be, or later become, known in the art, including, but not limited to, antiblocking agents, antistatic agents, slip agents, pro-heat stabilizers, antioxidants, pro-oxidant additives, pigments, plasticizers, etc.

Antiblocking agents act to prevent film layers from sticking to one another when wound into a roll or when packaged in contact with one another. Typical antiblocking substances include concentrates of silica or talc blended with a polymeric materials such as polyethylene or polycaprolactone. Reduction of blocking in the films of the present invention can also be obtained by loading the film surface with small particles or powders such as chalk, clay, silica,. starch and similar materials. Powdered polymeric materials (e.g. polytetrafluoroethylene) can also be used to reduce blocking when applied to the surface of films of the present invention. Such film surface treatments can be used to reduce blocking alone or in combination with other antiblock methods. The quantity of powder antiblock substance commonly added to the surface of a film, when used, is from about 0.5 g/m$^2$ to about 5 g/m$^2$.

Antistatic agents may be incorporated in films of the present invention; examples of such agents include ethoxylated amines and quarternary amine salts having organic constituents of about 12-18 carbon atoms in length. Agents of this type slowly defuse to the surface of the film and, because of their ionic character, form an electrically conductive layer on the surface of the film. Antistatic agents commonly constitute from about 1% to about 5% of the weight of the films, when used.

Slip agents may be incorporated into the films of the present invention to reduce drag over rollers and other forming equipment. Examples of such agents are those commonly derived from amides of fatty acids having about 12-22 carbon atoms. Such agents may augment the antiblocking properties of the films of the present invention. Such slip agents are commonly incorporated in films from about 0.05% to about 3% of the weight of the films when used.

In order to minimize degradation of the biodegradable films of the present invention during processing by extrusion or other techniques, heat stabilizers and antioxidants can be added to the polymer formulations. However, these types of additives may interfere with the biodegradation and compostability of the films if they are added at too high a level. Consequently, although many types of heat stabilizers, primary antioxidants, and secondary antioxidants are available, preferably no additional stabilizers are added to the blends of starch interpenetrated networks with aliphatic polyesters used in the films of the present invention.

In cases where an optional polyolefin constituent is included in the films of the current invention a pro-oxidant system may also be included to enhance the degradation of the polyolefin. Pro-oxidant systems are designed to reduce the molecular weights of polyolefins to a value of less than about 1000 whereupon the short oligomeric segments which remain can be further biodegraded by micro-organisms.

Pro-oxidant systems generally consist of multiple components including an antioxidant, which is active over a relatively short time period, and a latent pro-oxidant such as an organic salt of a transition metal. Other rapidly degrading additives such as chemically unsaturated polymers or copolymers or filler particles derived from natural products such as starches, proteins, cellulose, and sugars can also be included with the pro-oxidant system.

For example, U.S. Pat. No. 4,983,651, Griffin, issued Jan. 8, 1991, incorporated herein by reference, disclose degradable plastic compositions based on polyolefins blended with an antioxidant, starch, a styrene butadiene copolymer, and a transition metal organic salt. The transition metal is selected from the group Ca, Zn, Cu, Ag, Ni, Co, Fe, Mn, Cr, and V; and the organic salt is selected from the group consisting of stearates, oleates, behemates, myristates, erucates, linoleates, napthenates, acetonyl, acetonates, hydroxyquinolinates, and metalamine salt complexes. The transition metal salt complexes are used in quantities which will provide from about 0.001% to about 1.0% by weight of the metal in the composition.

The use of antioxidants together with transition metal salts as additives in polyolefins is also disclosed in British Patent GB 1,434,641 issued to Huels on May 5, 1976, and incorporated herein by reference. Polyolefin compositions are disclosed comprising 0.01–1.0% antioxidant, 0.02–1.0% of an organic copper salt, and 0.1–0.2% of an organic manganese, cobalt, or iron salt where the organic group is selected from the group oleates, palmitates, and stearates.

In a preferred embodiment of the present invention, the weight ratio of the destructurized starch component to the aliphatic polyester is greater than 1:1. Thus, for biodegradable films comprising a binary mixture of the aliphatic polyester and destructurized starch component, the films will contain more than 50% by weight of the destructurized starch component, more preferably from about 55% to about 90%, and most preferably, from about 60% to about 85%. Preferably, the films will also contain from about 5% to about 45% and, more preferably, from about 15% to about 40% of the aliphatic polyester.

The biodegradable films of the present invention may be processed using conventional procedures for producing films of blended polymers on conventional film making equipment. Pellets of the above described components can be first dry blended and then melt mixed in the film extruder itself. Alternatively, if insufficient mixing occurs in the film extruder, the pellets can be first dry blended and then melt mixed in a precompounding extruder followed by repelletization prior to film extrusion.

The polymer blends can be melt processed into films using either cast or blown film extrusion methods, both of which are described in "Plastics Extrusion Technology - 2nd. Ed." by Allan A. Griff (Van Nostrand Reinhold - 1976), incorporated by reference herein. Cast film is extruded through a linear slot die. Typically, the flat web is cooled on a large moving polished metal roll. It quickly cools, and peels of this first roll passes over one or more auxilary cooling rolls, then through a set of rubber-coated pull or "haul-off" rolls, and finally to a winder. A method of making a cast biodegradable film of the current invention suitable for use as a backsheet for an absorbent product is described hereinafter in Example I.

In blown film extrusion, the melt is extruded upward through a thin annular die opening. This process is also referred to as tubular film extrusion. Air is introduced through the center of the die to inflate the tube and causes it to expand. A moving bubble is thus formed which is held at constant size by control of internal air pressure. The tube of film is cooled by air blown through one or more chill rings surrounding the tube. The tube is next collapsed by drawing it into a flattening frame through a pair of pull rolls and into a winder. For backsheet applications, the flattened tubular film is subsequently slit open, unfolded and further slit into widths appropriate for use in absorbent products.

Film materials used as liquid impervious backsheets in absorbent articles, such as disposable diapers, typically have a thickness of from 0.01 mm to about 0.2 mm, preferably from 0.012 mm to about 0.051 mm.

In general, the liquid impervious backsheet is combined with a liquid pervious topsheet and an absorbent core positioned between the topsheet and the backsheet, optionally elastic members and tape tab fasteners. While the topsheet, the backsheet, the absorbent core and elastic members may be assembled in a variety of well known configurations, a preferred diaper configuration is described generally in U.S. Pat. No. 3,860,003, entitled "Contractible Side Portion for Disposable Diaper" which issued to Kenneth B. Buell on Jan. 14, 1975 and which patent is incorporated herein by reference.

The topsheet is compliant, soft-feeling, and non-irritating to the wearer's skin. Further, the topsheet is liquid pervious, permitting liquids to readily penetrate through its thickness. A suitable topsheet may be manufactured from a wide range of materials such as porous foams, reticulated foams, apertured plastic films, natural.. fibers (e.g., wood or cotton fibers), synthetic fibers (e.g., polyester or polypropylene fibers) or from a combination of natural and synthetic fibers. Preferably the topsheet is made of a hydrophobic material to isolate the wearer's skin from liquids in the absorbent core.

A particularly preferred topsheet comprises staple-length polypropylene fibers having a denier of about 1.5 such as Hercules type 151 polypropylene marketed by Hercules, Inc. of Wilmington, Del. As used herein, the term "staple-length fibers" refers to those fibers having a length of at least about 16 mm.

There are a number of manufacturing techniques which may be used to manufacture the topsheet. For example, the topsheet may be woven, nonwoven, spunbonded, carded, or the like. A preferred topsheet is carded, and thermally bonded by means well known to those skilled in the fabrics art. Preferably, the topsheet has a weight from about 18 to about 25 g/m$^2$, a minimum dried tensile strength of at least about 400 g/cm in the machine direction, and a wet tensile strength of at least about 55 g/cm in the cross-machine direction.

The topsheet and the backsheet are joined together in any suitable manner. As used herein the term "joined" encompasses configurations whereby the topsheet is directly joined to the backsheet by affixing the topsheet directly to the backsheet, and configurations whereby the topsheet is indirectly joined to the backsheet by affixing the topsheet to intermediate members which in turn are affixed to the backsheet. In a preferred embodiment, the topsheet and the backsheet are affixed directly to each other in the diaper periphery by attachment means such as an adhesive or any other attachment means as known in the art. For example, a uniform, continuous layer of adhesive, a patterned layer of adhesive, or an array of separate lines or spots of adhesive may be used to affix the topsheet to the backsheet.

Tape tab fasteners are typically applied to the back waistband region of the diaper to provide a fastening means for holding the diaper on the wearer. The tape tab fasteners can be any of those well known in the art, such as the fastening tape disclosed in U.S. Pat. No. 3,848,594, issued to Kenneth B. Buell on Nov. 19, 1974, the disclosure of which is incorporated herein by reference. These tape tab fasteners or other diaper fastening means are typically applied near the corners of the diaper.

Preferred diapers have elastic members disposed adjacent the periphery of the diaper, preferably along each longitudinal edge so that the elastic members tend to draw and hold the diaper against the legs of the wearer. The elastic members are secured to the diaper in an elastically contractible condition so that in a normally unrestrained configuration the elastic members effectively contract or gather the diaper. The elastic members can be secured in an elastically contractible condition in at least two ways. For example, the elastic members may be stretched and secured while the diaper is in an uncontracted condition. Alternatively, the diaper may be contracted, for example, by pleating, an elastic member secured and connected to the diaper while the elastic members are in their relaxed or unstretched condition.

The elastic members may take a multitude of configurations. For example the width of the elastic members may be varied from about 0.25 mm to about 25 mm or more; the elastic members may comprise a single strand of elastic material or the elastic members may be rectangular or curvilinear. Still further, the elastic members may be affixed to the diaper in any of several ways which are known in the art. For example the elastic members may be ultrasonically bonded, heat and pressure sealed into the diaper using a variety of bonding patterns, or the elastic members may simply be glued to the diaper.

The absorbent core of the diaper is positioned between the topsheet and backsheet. The absorbent core may be manufactured in a wide variety of sizes and shapes (e.g., rectangular, hour-glass, asymmetrical, etc.) and from a wide variety of materials. The total absorbent capacity of the absorbent core should, however, be compatible with the designed liquid loading for the intended use of the absorbent article or diaper. Further, the size and absorbent capacity of the absorbent core may vary to accommodate wearers ranging from infants through adults.

A preferred embodiment of the diaper has a modified hour-glass shaped absorbent core. The absorbent core is preferably an absorbent member comprising a web or batt of airfelt, wood pulp fibers, and a particulate absorbent polymeric composition disposed therein.

Other examples of absorbent articles according to the present invention are sanitary napkins designed to receive and contain vaginal discharges such as menses. Disposable sanitary napkins are designed to be held adjacent to the human body through the agency of a garment, such as an undergarment or a panty or by a specially designed belt. Examples of the kinds of sanitary napkins to which the present invention is readily adapted are shown in U.S. Pat. No. 4,687,478, entitled "Shaped Sanitary Napkin With Flaps" which issued to Kees J. Van Tilburg on Aug. 18, 1987 and in U.S. Pat. No. 4,589,876, entitled "Sanitary Napkin" which issued to Kees J. Van Tilburg on May 20, 1986, the disclosures of both patents being incorporated herein by reference. It will be apparent that the polymeric compostable films described herein may be used as the liquid impervious backsheet of such sanitary napkins. On the other hand it will be understood the present invention is not limited to any specific sanitary napkin configuration or structure.

In general, sanitary napkins comprise a liquid impervious backsheet, a liquid pervious topsheet, and an absorbent core placed between the backsheet and the topsheet. The backsheet comprises one of the compostable films containing a blend of polymeric components as described above. The topsheet may comprise any of the topsheet materials discussed with respect to diapers.

Importantly, the absorbent articles according to the present invention are compostable to a greater extent than conventional absorbent articles which employ a polyolefin, typically a polyethylene backsheet.

The term "compostable" as used herein means a material that meets the following three requirements: (1) is capable of being processed in a composting facility for solid waste; (2) if so processed will end up in the final compost; and (3) if the compost is used in the soil the material will ultimately biodegrade in the soil.

A polymer film material present in solid waste submitted to a composting facility for processing does not necessarily end up in the final compost. Certain composting facilities subject the solid waste stream to air classification prior to further processing, in order to separate piper and other materials. A polymer film would most probably be separated from the solid waste stream in such an air classification and therefore not be processed in the composting facility. Nevertheless, it may still be a "compostable" material according to the above definition because it is "capable" of being processed in a composting facility.

The requirement that the material ends up in the final compost typically means that it undergoes a form of degradation in the composting process. Typically, the solid waste stream will be subjected to a shredding step in an early phase of the composting process. As a result, the polymer film will be present as shreds rather than a sheet. In the final phase of the composting process, the finished compost will be subjected to a screening step. Typically, the polymer shreds will not pass through the screens if they have retained the size they had immediately after the shredding step. The compostable materials of the present invention will have lost enough of their integrity during the composting process to allow semidegraded shreds to pass through the screens. However, it is conceivable that a composting facility might subject the solid waste stream to a very rigorous shredding and a rather coarse screening, in which case nondegradable polymers like polyethylene would meet requirement (2). Therefore, meeting requirement (2) is not enough for a material to be compostable within the present definition.

What does distinguish the compostable material as defined herein from materials like polyethylene is requirement (3) that they ultimately biodegrade in the soil. This biodegradation should be complete to $CO_2$ and water. This biodegradability requirement is not essential to the composting process or the use of composting soil. Solid waste and the compost resulting therefrom may contain all kinds of nonbiodegradable materials, for example, sand. However, to avoid a build up of man-made materials in the soil, it is required herein that such materials be fully biodegradable. By the same token, it is not at all necessary that this biodegradation be fast. As long as the material itself and intermediary decomposition products are not toxic or otherwise harmful to the soil or the crops, it is fully acceptable that their biodegradation takes several months or even years, since this requirement is present only to avoid an accumulation of man-made materials in the soil.

The following examples illustrate the practice of the present invention but are not intended to be limiting thereof.

EXAMPLE I

A 30:70 by weight dry blend of TONE P-787 polycaprolactone to Mater-Bi Grade SA007 is prepared by adding 7.5 pounds of TONE pellets to 17.5 pounds Mater-Bi in a Kelly Duplex Mixer and mixing for 15 minutes.

The dry blend is then melt compounded to 150° C. in a Brabender twin screw compounder equipped with an eight port strand die. The molten strands are cooled and solidified in a water bath prior to entering a Cumberland Quietizer Pelletizer where each strand is chopped into pellets approximately 0.125 inches long.

The pellets are converted into a film approximately 0.0012 inches thick using a 30 mm diameter single screw extruder (Zahnradwerk Kollman) equipped with standard polyolefin-type screw and a 24 inch wide coathanger die. The temperature of the extruder barrel varies from about 127° C. in the feed zone to about 132° C. at the discharge end near the die. The die temperature is maintained at about 138° C. Film takeoff and winding is accomplished on a Johnson takeoff system. The chill rolls on which the film is cooled and solidified are maintained at about 21° C. After cooling, the thick edges of the film are slit off and removed and the final film approximately 13.5 inches wide, is collected on a 3 inch diameter cardboard core.

The resulting film is translucent and displays excellent toughness and mechanical strength. These proper-

EXAMPLE II

A 66:17:17 by weight dry bland of Mater-Bi SA007, TONE P-787, and an ethylene-acrylic acid copolymer (DOW PRIMACOR 3460) is prepared by combining 16.5 pounds Mater-Bi, 4.25 pounds TONE, and 4.25 pounds PRIMACOR pellets in a Kelly Duplex Mixer and mixing for 30 minutes.

The dry blend is then melt compounded on a Brabender twin screw compounder equipped with an eight port strand die. The compounder barrel temperature is maintained between 155 and 160° C., and the die maintained at about 145° C. The strands are cooled in a water bath and pelletized as described in Example I.

The pellets are converted into a film ranging from about 0.0012 to about 0.0014 inches thick using the same extruder and takeoff equipment described in Example I. Die temperatures and takeoff conditions are the same. The resulting film, after slitting to about 13.5 inches wide, is wound onto a 3 inch diameter cardboard core.

EXAMPLE III

A disposable baby diaper according to this invention is prepared as follows. The dimension listed are for a diaper intended for use with a child in the 6–10 kilogram size range. These dimensions can be modified proportionately for different size children, or for adult incontinence briefs, according to standard practice.

1. Backsheet: 0.020–0.038 mm film consisting of a 30:70 polycaprolactone to Mater-Bi blend (prepared as described in Example I); width at top and bottom 33 cm; notched inwardly on both sides to a width-at-center of 28.5 cm; length 50.2 cm.

2. Topsheet: carded and thermally bonded staple-length polypropylene fibers (Hercules type 151 polypropylene); width at top and bottom 33 cm; notched inwardly on both sides to a width-at-center of 28.5 cm; length 50.2 cm.

3. Absorbent core: comprises 28.6 g of cellulose wood pulp and 4.9 g of absorbent gelling material particles (commercial polyacrylate from Nippon Shokubai); 8.4 mm thick, calendered; width at top and bottom 28.6 cm; notched inwardly at both sides to a width-at-center of 10.2 cm; length 44.5 cm.

4. Elastic leg bands: four individual rubber strips (2 per side); width 4.77 mm; length 370 mm; thickness 0.178 mm (all the foregoing dimensions being in the relaxed state).

The diaper is prepared in standard fashion by positioning the core material covered with the topsheet on the backsheet and gluing.

The elastic bands (designated "inner" and "outer", corresponding to the bands closest to, and farthest from, the core, respectively) are stretched to ca. 50.2 cm and positioned between the topsheet/backsheet along each longitudinal side (2 bands per side) of the core. The inner bands along each side are positioned ca. 55 mm from the narrowest width of the core (measured from the inner edge of the elastic bank). This provides a spacing element along each side of the diaper comprising the flexible topsheet/backsheet material between the inner elastic and the curved edge of the core. The inner bands are glued down along their length in the stretched state. The outer bands are positioned ca. 13 mm from the inner bands, and are glued down along their length in the stretched state. The topsheet/backsheet assembly is flexible, and the glued-down bands contract to elasticize the sides of the diaper.

EXAMPLE IV

A lightweight pantiliner suitable for use between menstrual periods comprises a pad (surface area 117 cm$^2$; SSK air felt 3.0 g) containing 1.0 g of absorbent gelling material particles (commercial polyacrylate; Nippon Shokubai); said pad being interposed between a porous formed-film topsheet according to U.S. Pat. No. 4,463,045 and a backsheet which comprises a 0.03 mm thickness polycaprolactone/Mater-Bi (70:30 weight basis) film, as prepared in accordance with Example I.

EXAMPLE V

A catamenial product in the form of a sanitary napkin having two flaps extending outward from its absorbent core is prepared using a pad in the manner of Example IV (surface area 117 cm$^2$; 8.5 g SSK air felt), per the design of U.S. Pat. No. 4,687,478, Van Tillburg, Aug. 18, 1987. The backsheet and topsheet materials are the same as described in Example IV.

EXAMPLE VI

The diaper of Example III is modified by replacing the backsheet with a backsheet consisting of a 0.020 to 0.038 mm thickness film comprising a 66:17:17 Mater-Bi: Tone: ethylene-acrylic acid copolymer blend (prepared as described in Example II).

From the foregoing specification, one skilled in the art can easily ascertain the essential characteristics of this invention, and without departing from the spirit and scope thereof, may make various changes and modifications to adapt the invention to various usages and conditions not specifically mentioned herein. The scope of this invention shall be defined by the claims which follow.

What is claimed is:

1. A biodegradable liquid impervious film comprising a blend of:
   (a) a biodegradable interpenetrated network of destructurized starch and a copolymer selected from the group consisting of ethylene acrylic acid copolymer and ethylene vinyl alcohol copolymer; and
   (b) a biodegradable aliphatic polyester, the weight ratio of said interpenetrated network of destructurized starch and copolymer to said aliphatic polyester being greater than 1:1.

2. The biodegradable film of claim 1 wherein the film comprises from about 55% to about 95% by weight of said interpenetrated network of destructurized starch and copolymer, and from about 5% to about 45% by weight of the aliphatic polyester.

3. The biodegradable film of claim 2 wherein less than 40% of the starch in the film is free and in the form of particles having an average number diameter below 1 micrometer.

4. The biodegradable film of claim 1 wherein the copolymer is an ethylene/acrylic acid copolymer.

5. The biodegradable film of claim 4 wherein the copolymer has an acrylic acid content of from about 3% to about 30% by weight.

6. The biodegradable film of claim 1 wherein the copolymer is an ethylene/vinyl alcohol copolymer.

7. The biodegradable film of claim 6 wherein the copolymer has a vinyl alcohol content of from about 50% to about 80 mole %.

8. The biodegradable film of claim 2 wherein the film comprises from about 60% to about 85% by weight of the interpenetrated network of destructurized starch and copolymer, and from about 15% to about 40% by weight of the aliphatic polyester.

9. The biodegradable film of claim 8 wherein less than 20% of the starch in the film is free and in the form of particles having an average number diameter below 1 micrometer.

10. The biodegradable film of claim 1 wherein the aliphatic polyester is polycaprolactone.

11. The biodegradable film of claim 1 wherein the aliphatic polyester is the oxidation product of an ethylene-carbon monoxide copolymer and a peroxyacid oxidizing agent.

12. The biodegradable film of claim 1 wherein the aliphatic polyester is a polyhydroxybutyrate-valerate copolymer having a valerate content-from about 10 to about 24 mole %.

13. The biodegradable liquid impervious film of claim 1, wherein the aliphatic polyester is an aliphatic polyester-based polyurethane.

* * * * *